United States Patent [19]

Barton et al.

[11] Patent Number: 4,621,156

[45] Date of Patent: Nov. 4, 1986

[54] OPTICAL FILTER AGENTS AND PHOTOGRAPHIC PRODUCTS AND PROCESSES CONTAINING SAME

[75] Inventors: Derek H. R. Barton, Gif-sur-Yvette, France; Irena Y. Bronstein-Bonte, Newton; Lloyd D. Taylor, Lexington, both of Mass.

[73] Assignee: Polaroid Corporation, Cambridge, Mass.

[21] Appl. No.: 309,914

[22] Filed: Oct. 8, 1981

Related U.S. Application Data

[62] Division of Ser. No. 89,559, Oct. 29, 1979, Pat. No. 4,298,676.

[51] Int. Cl.$^4$ .................................... C07C 109/12

[52] U.S. Cl. .................................... 564/250; 564/251

[58] Field of Search .................................... 564/250, 251

[56] References Cited

U.S. PATENT DOCUMENTS

| | | | |
|---|---|---|---|
| 3,414,650 | 12/1968 | Catino et al. | 564/250 X |
| 3,826,844 | 7/1974 | Moon | 564/251 X |
| 3,923,506 | 12/1975 | Bergfjord et al. | 564/251 X |
| 3,943,132 | 3/1976 | Schirmann et al. | 564/251 X |
| 4,258,181 | 3/1981 | Murdock et al. | 564/251 X |

*Primary Examiner*—Robert V. Hines

*Attorney, Agent, or Firm*—Louis G. Xiarhos

[57] ABSTRACT

Optical filter agents and photographic products and processes using same are disclosed. The optical filter agents are pH-sensitive hydrazone compounds conforming to the following structural formula:

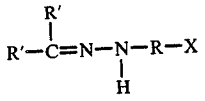

where R is any group which can provide a double bond for conjugation with the

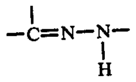

portion of the compound to provide light-absorbing capability or color for the agent at a pH above its pKa, X is a substituent of R providing at least one electron-withdrawing group and each R′ can be defined as any substituent that does not impair the light-absorbing capacity of the compound at a pH above the pKa thereof. The pH-sensitive optical filter agents have a highly colored light-absorbing form at a pH above the pKa and are substantially non-absorbing at a pH below the pKa. The pH-sensitive optical filter agents are useful in photographic film units and processes for the protection of photoexposed photosensitive elements against the occurrence of fogging during in-light development.

15 Claims, 3 Drawing Figures

OPTICAL FILTER AGENTS AND PHOTOGRAPHIC PRODUCTS AND PROCESSES CONTAINING SAME

This is a division of application Ser. No. 089,559, filed Oct. 29, 1979, now U.S. Pat. No. 4,298,676, issued Nov. 3, 1981.

BACKGROUND OF THE INVENTION

1. The Field of the Invention

This invention relates to photographic products and processes and particularly to diffusion transfer photographic products and processes.

2. Description of the Prior Art

Diffusion transfer photographic products and processes are known to the art and details relating to them can be found in U.S. Pat. Nos. 2,983,606; 3,415,644; 3,415,645; 3,415,646; 3,473,925; 3,482,972; 3,551,406; 3,573,042; 3,573,043; 3,573,044; 3,576,625; 3,576,626; 3,578,540, 3,569,333; 3,579,333; 3,594,164; 3,594,165; 3,597,200; 3,647,437; 3,672,486; 3,672,890; 3,705,184; 3,752,836; 3,857,865 and British Pat. No. 1,330,524.

Essentially, diffusion transfer photographic products and processes involve film units having a photosensitive system including at least one silver halide layer usually integrated with an image-providing material. After photoexposure, the photosensitive system is developed to establish an imagewise distribution of a diffusible image-providing material, at least a portion of which is transferred by diffusion to an image-receiving element having a layer capable of mordanting or otherwise fixing the transferred image-providing material. In some diffusion transfer products, the transfer image is viewed by reflection after separation of the image-receiving element from the photosensitive system. In other products, however, such separation is not required and, instead, the transfer image in the image-receiving layer is viewed against a reflecting background usually provided by a dispersion of white, light-reflecting pigment—such as titanium dioxide.

Diffusion transfer photographic products providing a dye image viewable against a reflecting background without separation are oftentimes referred to in the art as "integral negative-positive film units" and such units are of two general types. Integral negative-positive film units of a first type are described, for example, in the above-noted U.S. Pat. No. 3,415,644. Such film units include a photosensitive system and associated dye image-providing material carried on an opaque support, an image-receiving layer carried on a transparent support and means for distributing a processing composition between the elements of the film unit. Photoexposure is made through the transparent support and image-receiving layer and a processing composition which includes a reflecting pigment is distributed between the image-receiving and photosensitive components. After distribution of the processing composition and before processing is complete, the film unit can be—and usually is—transported into conditions of ambient light to permit in-light processing.

Accordingly, in integral negative-positive film units of this type, the layer provided by distributing the reflecting pigment must be capable of performing certain functions. For example, the distributed reflecting layer must be able to provide at least partial protection against further exposure of the photoexposed element if the film unit is transported into ambient light conditions before processing is completed. At the same time, however, the layer must be sufficiently permeable to permit effective transfer of image dyes from the photoexposed photosensitive layer or layers to the image-receiving layer. Moreover, after transfer, the layer must provide a reflecting background of suitable efficiency for viewing the dye image transferred to the image-receiving layer. Also, in film units of this type, the reflecting layer should effectively mask the photoexposed photosensitive layer or layers.

Integral negative-positive film units of a second type, as described, for example, in U.S. Pat. No. 3,594,165, include a transparent support, carrying the appropriate photosensitive layers and associated image dye-providing materials, a permeable opaque layer, a permeable light-reflecting pigment-containing layer, an image-receiving layer viewable through a transparent support against the light-reflecting layer, and means for distributing a processing composition between the photosensitive layer and a transparent cover or spreader sheet. Additionally, integral negative-positive film units of this second type include an opaque processing composition which is distributed after photoexposure to provide a second opaque layer which can prevent additional exposure of the photosensitive element.

In film units of this second type, exposure is made through the transparent cover sheet. After distribution of the processing composition and installation of the second opaque layer, this type of film unit can also be transported into light before processing is complete. Accordingly, in film units of this second type, the light-reflecting pigment-containing layer may also perform the functions of providing at least partial protection for the photoexposed element until processing is complete but, again, this layer must permit effective transfer of image dyes to the image-receiving layer. Also, like the film units of the "first type", the layer must provide a suitable reflecting background for viewing the dye image transferred to the image-receiving layer. Moreover, effective masking of the photoexposed photosensitive layer must also be achieved for film units of this "second type".

In many known integral negative-positive film units, temporary opacification systems have been used in combination with light-reflecting layers and light-reflecting layer materials. These temporary opacification systems are desiged to cooperate with the reflecting layer and/or reflecting layer materials to provide sufficient opacity to prevent further exposure of the film unit through the reflecting layer during processing of the film unit in light.

U.S. Pat. No. 3,647,437, for example, describes a temporary opacification system that has been used extensively in commercial integral negative-positive film units of the first type, e.g., film units of the type described in U.S. Pat. No. 3,415,644. That temporary opacification system essentially involves a pH-sensitive agent which can absorb light at one pH but is rendered substantially non-light absorbing at another pH. As disclosed in U.S. Pat. No. 3,647,437, the optical filter agent is usually dispersed in the film unit's processing composition together with a light-reflecting pigment. In turn, the processing composition is integrated with elements of the film unit so that the composition can be distributed between the photoexposed photosensitive layer or layers and the image-receiving layer. Accordingly, after distribution of the processing composition, an opaque layer comprising the reflecting pigment and optical filter agent is provided and the opaque layer covers a major surface of the photoexposed layer. This light-absorbing filter agent cooperates with the reflecting pigment to provide a reflecting layer having a degree of opacity sufficient to prevent photoexposure through the layer. As development and transfer of dye image material proceeds, the pH of the film unit changes so that the light-absorbing capability of the pH-sensitive optical filter agent is reduced until it becomes substantially non-light absorbing and its opacity-providing function is diminished. When processing is complete, the reflecting layer—now comprising the reflecting pigment and decolorized optical filter agent—provides a white background for viewing the dye image and for masking the developed photoexposed layers.

Additional details relating to pH-sensitive optical filter agents useful in diffusion transfer photographic products and processes can be found in U.S. Pat. Nos. 3,702,244 and 3,702,245 among others.

SUMMARY OF THE INVENTION

This invention presents to the art a new class of pH-sensitive optical filter agents and novel photographic products and processes using them. The pH-sensitive optical filter agents used in film units of this invention are hydrazone compounds which conform to the following structural formula:

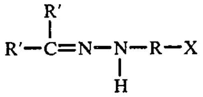

where R is any group which can provide a double bond for conjugation with the

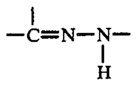

portion of the compound to provide light-absorbing capability or color for the agent at a pH above its pKa, X is a substituent of R providing at least one electron-withdrawing group and each R' can be defined as any substituent that does not impair the light-absorbing capacity of the compound at a pH above the pKa thereof.

According to this invention, hydrazones of the structure described above are particularly suitable for protecting photoexposed diffusion transfer film units from fogging that can occur during development of the film unit in light. These hydrazones can absorb radiation within wavelength ranges of the visible spectrum and individual hydrazones or combinations of them alone or with other known pH-sensitive optical filter agents can be employed to provide absorption effective over a preselected range or region of the visible spectrum.

The pH-sensitive optical filter agents of this invention are pH-sensitive indicator dyes possessing spectral absorption characteristics which can be reversibly altered in response to changes in pH. The compounds have a highly colored form capable of absorbing visible radiation at a pH above the pKa of the compound. However, the light-absorbing capability of the compounds is substantially reduced (at least in the visible region) at a pH below the pKa of the compound with the result that the compounds are substantially in a non-light absorbing form. For the purposes of this invention, pKa means the pH at which about 50% of the compound is present in its light-absorbing form and about 50% is present in its non-light absorbing form.

Hydrazones comprising the structure described above are believed to undergo the following changes in the presence of hydrogen and hydroxyl ions:

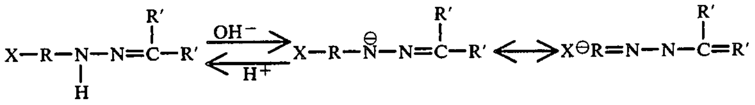

The invention, as well as details relating to the manners of making and using it, will be more fully appreciated by reference to the following description of the preferred embodiments taken in connection with FIGS. 1 to 3.

DESCRIPTION OF THE PREFERRED EMBODIMENTS

The preferred film units of the present invention are integral negative-positive film units of the type described in such patents as U.S. Pat. Nos. 3,415,644 and 3,647,437.

Figure 1:
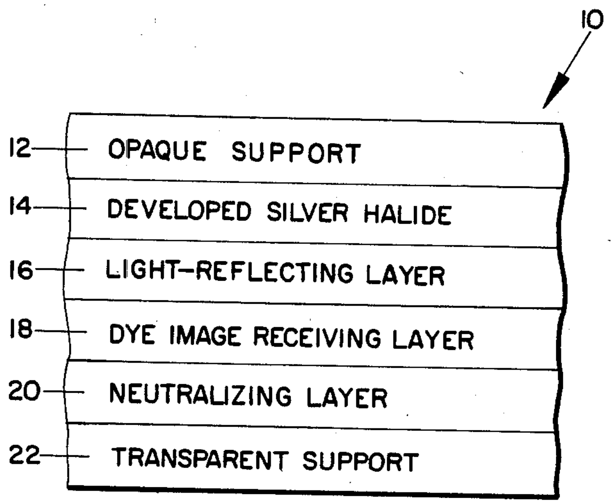
FIG. 1 is a simplified or schematic view of an arrangement of essential elements of preferred film units of the present invention, shown after exposure and processing.

Referring now to FIG. 1, there is shown a film unit of the type referenced in U.S. Pat. Nos. 3,415,644 and 3,657,437 following exposure and processing. The film unit 10 includes opaque support 12 carrying a photosensitive system 14 and a light-reflecting layer 16 comprising a light-reflecting pigment and a pH-sensitive optical filter agent of this invention. Initially, the mixture of light-reflecting pigment and the optical filter agent are dispersed in an aqueous alkaline photographic processing composition retained in a rupturable container (not shown). After photoexposure of photosensitive system 14 through transparent support 22 and image-receiving layer 18, the processing composition is distributed between layers 14 and 18.

When the processing composition is distributed over photosensitive layer 14, a light-reflecting layer 16 comprising the mixture of the light-reflecting pigment and pH-sensitive optical filter agent of this invention is provided between image-receiving layer 18 and photosensitive layer 14. During at least the initial stage or stages of processing, this layer is subjected to an environmental pH which is above the pKa of the optical filter agent, and under such pH conditions, the optical filter agent is light absorbing. Accordingly, during this stage of processing, the light-absorbing optical filter agent cooperates with the light-reflecting pigment to provide a layer presenting sufficient opacity to protect the photosensitive system of layer 14 from further photoexposure through transparent support 22. The processing composition initiates development of photoexposed photosensitive layer or layers 14 in manners well known to the art to establish an imagewise distribution of diffusible image-providing material which can comprise silver and/or one or more dye image-providing materials. The diffusible, image-providing material is transferred through permeable, light-reflecting layer 16 where it is mordanted, precipitated or otherwise retained in known manner in or on image-receiving layer 18 to provide a transfer image viewable through transparent support 22 against light-reflecting layer 16.

Film units of the type shown in FIG. 1 include means to reduce the pH of the film unit to a predetermined level. The means to effect this reduction in pH is shown in FIG. 1 as a substantially transparent polymeric acid, neutralizing layer 20 of the type described in U.S. Pat. No. 3,415,644. Preferably, the polymeric acid neutralizing layer 20 is used in combination with a spacer or timing layer (not shown) positioned between polymeric acid neutralizing layer 20 and image-receiving layer 18.

Polymeric acid neutralizing layer 20 is designed to function after distribution of the aqueous alkaline processing composition. After a predetermined period, alkaline reagents diffusing to and contacting polymeric acid layer 20 will be neutralized. This neutralization continues until the environmental pH of the film unit is reduced to a predetermined value—preferably to a pH of about 5 to 8. In any event, the neutralization is sufficient to at least reduce the environmental pH of the optical filter agent to a pH below the pKa value of the optical filter agent in layer 16. At this reduced pH, the light-absorbing capability of the pH-sensitive optical filter agent is reduced and becomes substantially non-absorbing of visible light. Accordingly, the finished processed film unit has a light-reflecting layer 16 which comprises the light-reflecting pigment and the optical filter agent in its substantially non-light absorbing form. Layer 16, therefore, provides a background for viewing the image in layer 18 through transparent polymeric acid layer 20 and transparent support 22. Also, layer 16 effectively masks photoexposed photosensitive layer(s) 14.

Suitable photosensitive systems employed in the film units described above are well known to the art and they include those providing silver images as well as color and multicolor images, as set forth in detail in the various patents cross-referenced here. The most preferred systems are multilayer systems involving a blue-, a green- and a red-sensitive silver halide layer integrated respectively with a yellow, a magenta, and a cyan dye image-providing material.

The hydrazone compounds suitable herein as pH-sensitive optical filter agents are hydrazones which are at least slightly, and preferably substantially, soluble in aqueous alkaline processing compositions and which conform to the following structural formula:

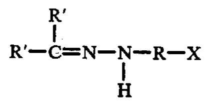

where R, X and R′ are as defined before.

Preferred R groups or radicals are those providing a carbon-to-carbon double bond (—C=C—) for the requisite conjugation. Representative preferred R groups or radicals can be illustrated by the following structural formula:

$$-\!\left[C=C-R^2\right]\!-X$$

where $R^2$ represents a divalent hydrocarbon moiety such as an acyclic, saturated or unsaturated, branched or unbranched hydrocarbon structure such as a divalent hydrocarbon moiety which is or can include a saturated or unsaturated carbocyclic ring structure. Alternatively, $R^2$ can be a moiety which is or can include a carbocyclic or a heterocyclic ring structure. X, as mentioned, represents at least one electron-withdrawing group attached to at least one of the carbon or hetero atoms of the R group or radical.

Preferred R groups or radicals, shown with an attached electron-withdrawing group, X, are those conforming to the following structural formula:

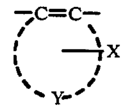

where Y represents the atoms necessary to complete a carbocyclic or heterocyclic ring structure having carbocyclic or heterocyclic rings or mixtures of such rings. Especially preferred R groups or radicals are the divalent aromatic radicals, e.g., phenylene, biphenylene, tetraphenylene, naphthylene and the like. Heterocyclic R radicals suitable herein are those wherein Y comprises the atoms necessary to complete the heterocyclic ring structure. Thus, radicals derived from furan, pyran, imidazole, pyrrole, carbazole or the like can be suitably employed as R radicals where such radicals provide a double bond for conjugation with the

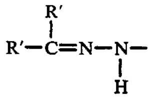

portion of the optical filter agent and provision of color or light-absorbing capability above the pKa of the optical filter agent and where the optical filter agent is rendered substantially colorless at a predetermined pH below the pKa thereof.

Broadly, suitable X substituents of R in the above formulae may be any electron-withdrawing group having a positive sigma value as defined by Hammett's Equation and capable of providing a stable anionic resonating structure. Such groups are well known to the art and exemplary Hammett values and procedures for their determination are set forth by J. Hine in Physical Organic Chemistry, 2nd Edition, p. 87, published in 1962; by H. VanBekkum, P. E. Verkade and B. M. Wepster in Rec. Trav. Chim. Volume 78, Page 815, published in 1959; by P. R. Wells in Chem. Revs., Volume 63, Page 171, published in 1963; by H. H. Jaffe, Chem. Revs., Volume 53, Page 191, published in 1953; by M. J. S. Dewar and P. J. Grisdale in J. Amer. Chem. Soc., Volume 84, Page 3548, published in 1962; and by Barlin and Perrin in Quart. Revs., Volume 20, Page 75 et seq., published in 1966. Suitable X groups herein include, for example, nitro, carboxy, trifluoromethyl, sulfonyl ($-SO_2-R^3$ where $R^3$ may be halogen, alkyl, aryl, alkaryl acyl and their substituted derivatives, particularly their halogen-substituted derivatives and especially their fluoro substituted derivatives).

An especially preferred class of hydrazones in the practice of this invention are those having the following structural formula:

FORMULA 1.

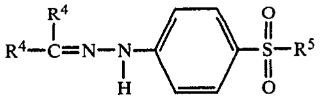

where each $R^4$ represents the same or different substituent and can be hydrogen or a saturated or unsaturated cyclic or acyclic hydrocarbon radical including substituted derivatives of such radicals, or both $R^4$ substituents together can provide a staturated or unsaturated cyclic or polycyclic radical, preferably a carbocyclic radical attached to the

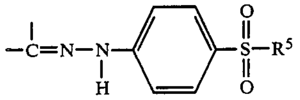

portion of the compound or one or both of $R^4$ can represent radicals preferably hydrocarbon radicals, linking together one or more

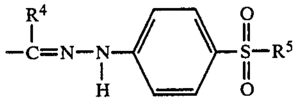

moieties; and $R^5$ is a saturated or unsaturated cyclic or acyclic hydrocarbon radical such as alkyl, aryl, araalkyl, alkaryl or the like, and substituted derivatives of such radicals especially halogen-substituted derivatives of these radicals, or $R^5$ can be the

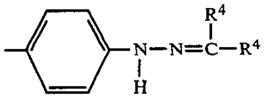

moiety.

Preferred $R^4$ radicals include alkyl radicals of from 1 to 6 carbon atoms (e.g., methyl, ethyl, hexyl); aryl radicals (e.g., phenyl or naphthyl); substituted-alkyl groups (e.g., alkyl groups of from 1 to 6 carbon atoms substituted with a nitro- or hydroxyl-group); or the radical

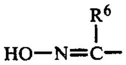

where $R^6$ is alkyl of from 1 to 6 carbon atoms (e.g., the radical

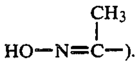
).

Hydrazones of the above Formula 1 are believed to be novel and specific hydrazones of this Formula include the following:

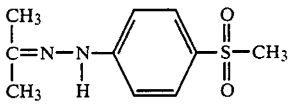

A.

mp = 178-180° C.

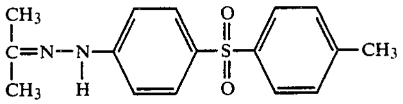

B.

mp = 166-168° C.

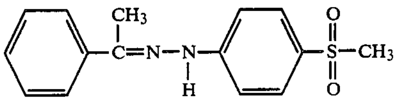

C.

mp = 210-212° C.

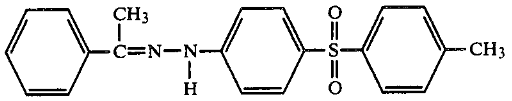

D.

mp = 173-175° C.

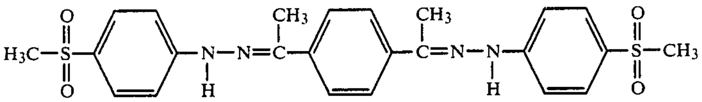

E.

mp = 240° C.

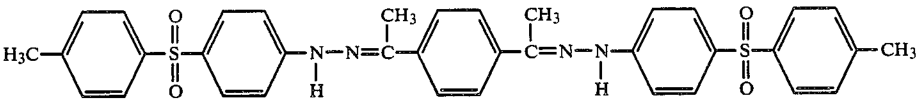

F.

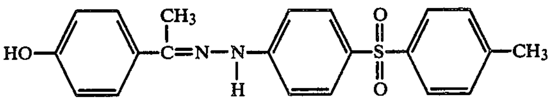

G.

-continued

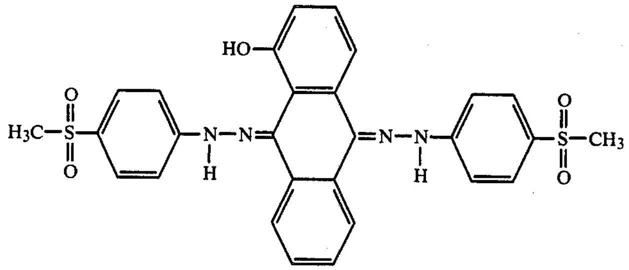

H.

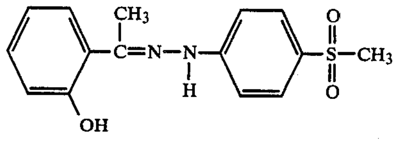

I.

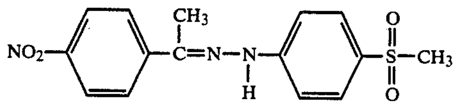

J.

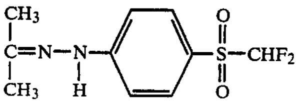

K.

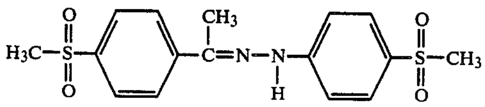

L.

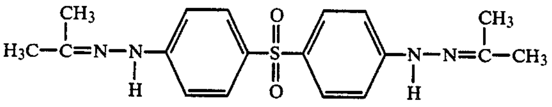

M.

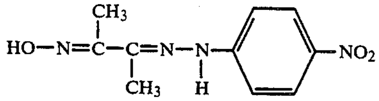

Other hydrazones not specifically within the above Formula 1 but useful in the practice of this invention are those of the following illustrative structures:

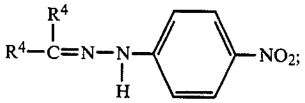

; and

O.

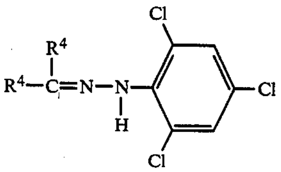

P.

where each $R^4$ has the meaning hereinbefore ascribed.

The hydrazone optical filter agents of the present invention can be suitably prepared by reaction of a hydrazine with a compound having one or more carbonyl groups and including aldehydes and ketones. Suitable hydrazine compounds for reaction with an aldehyde or ketone and provision of a hydrazone optical filter agent include those having the formula

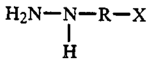

where R and X have the meanings set forth hereinbefore. Preferred hydrazine compounds for the provision of optical filter agents herein are those conforming to the following structure:

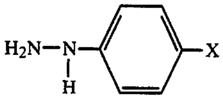

wherein X is an electron-drawing group as hereinbefore defined. Examples of hydrazine compounds useful herein include the following:

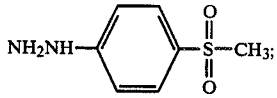

;

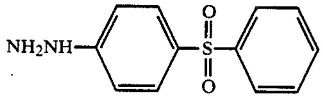

;

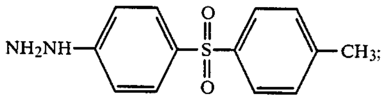

;

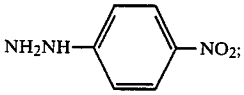

;

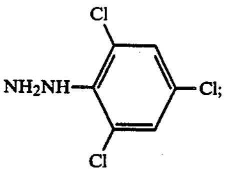

;

-continued

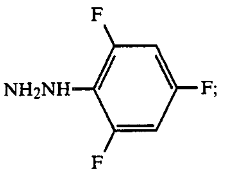

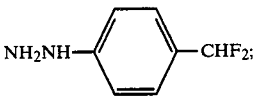

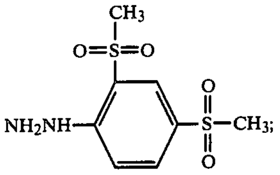

and

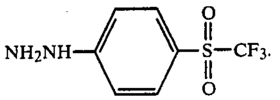

The hydrazone optical filter agents of the present invention can be suitably prepared by reaction of a hydrazine compound as hereinbefore described with an aldehyde or ketone corresponding to the formula

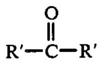

wherein each R′ represents a group or radical which does not impair the light-absorbing capability of the resulting hydrazone compound at a pH above the pKa thereof. Each R′ can represent the radicals or moieties as defined hereinbefore and particularly as defined in connection with groups $R^4$. Thus, R′ can, for example, be hydrogen or a saturated or unsaturated cyclic or acyclic hydrocarbon radical. Alternatively, each R′ can together with additional atoms comprise part of a carbocyclic or heterocyclic radical. Moreover, one or both R′ groups can represent radicals, preferably hydrocarbon, linking one or more hydrazone moieties. As is indicated hereinbefore, each R′ or $R^4$ group can be substituted with one or more substituent groups. Thus, solubilizing groups can, for example, be present as substituents on the ketone or aldehyde reactant as a means of promoting solubility of the resulting hydrazone optical filter agent in an alkaline processing composition or other medium. Suitable solubilizing groups include, for example, oxime groups. Other substituent groups can, however, be employed provided that such substituents are non-interfering with respect to the capacity of the resulting hydrazone derivative to exhibit light-absorbing properties above the pKa thereof. In addition, one or more R′ groups can be substituted with a keto groups such as to provide, for example, a diketone capable of reaction with two moles of hydrazine.

Examples of aldehyde and ketone compounds suitable for reaction with a hydrazine as hereinbefore described include acetone; benzophenone; p-diacetylbenzene; m-diacetylbenzene; 1-hydroxyanthroquinone; 2-hydroxyacetophenone; 4-hydroxyacetophenone; 4-nitroacetophenone; 4-methylsulfonyl acetophenone; benzaldehyde; 2-nitrobenzaldehyde; and 4-trifluoromethylsulfonyl)phenyl benzaldehyde; methyl trifluoromethyl ketone; di(trifluoromethyl)ketone; and diketones such as

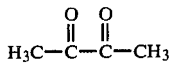 and 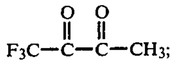

and mono-oximes of alkanediones such as the mono-oxime of 2,3-butanedione.

The hydrazone optical filter agents of the present invention can be provided by a suitably catalyzed reaction a hydrazine compound with an aldehyde or ketone as hereinbefore described. From the standpoint of rate of reaction, the employment of a catalyst, such as a mineral or other acid, will be employed. Acetic acid is preferred and permits the convenient production of the desired hydrazone compounds. In conducting the reaction of a hydrazine and an aldehyde or ketone, it will be preferred to employ the hydrazine compound in an amount substantially equivalent with the available functional carbonyl content of the aldehyde or ketone. The reactants can be employed in a suitable solvent such as ethanol and brought to boiling. A catalyst such as acetic acid is added and additional solvent, where needed, can be added to obtain a solution of reactants. Upon cooling, the hydrazone is precipitated and recovered, as by filtration. In the event the hydrazone does not separate upon cooling, the reaction mixture can be heated to boiling, water added until a cloudy reaction mixture is obtained and ethanol added to clarify the reaction mixture. The hydrazone recovered upon cooling can be recrystallized from a water-ethanol mixture.

The provision of a pH-sensitive optical filter agent of the invention by reaction of a hydrazine compound with an aldehyde or ketone can be illustrated by the following simplified general reaction scheme:

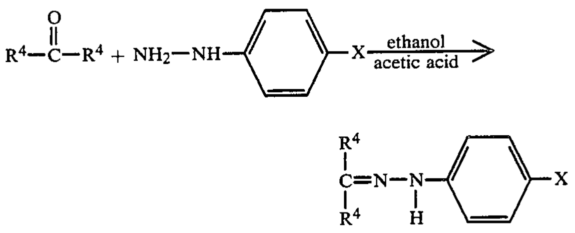

where $R^4$ and X have the meanings aforedescribed.

The pH-sensitive optical filter agents of this invention are preferably used in diffusion transfer film units as pH-sensitive optical filter agents or indicator dyes and manners of using them are known to the art. As mentioned, the primary function of optical filter agents is to provide temporary opacification during processing of a photoexposed film unit. In turn, this function must be accomplished without interfering with photoexposure of photosensitive layer(s) or with viewing the final image. Accordingly, the optical filter agents of this invention can be utilized in a layer of the film unit between the photosensitive layer(s) and a layer through which the photosensitive layer(s) is exposed. When employed in such a layer, the optical filter agent should be maintained at a pH at which the agent is substantially non-light absorbing. After photoexposure, and as the aqueous alkaline processing composition is applied to the optical filter agent-containing layer, the optical filter agent will be rapidly converted to a light-absorbing form (colored) to assume its opacification function. If the optical filter agent-containing layer is positioned so that it may interfere with viewing the image, the agent can be converted in known manners—to the non-light absorbing form. If conversion means are not available, the optical filter agent-containing layer should be positioned so that the layer is hidden after image formation. For example, the layer can be hidden by the reflecting layer masking the photoexposed layers.

In a preferred practice of this invention, the pH-sensitive optical filter agent is included in the aqueous alkaline processing composition with the light-reflecting pigment or agent. In this embodiment, the optical filter agent is light-absorbing (colored) in the distributed processing composition providing the light-reflecting layer and remains sufficiently light-absorbing during formation of the image to provide the degree of opacification required of the distributed light-reflecting layer. Thereafter, the optical filter agent is converted to a form exhibiting a substantially reduced light-absorbing capacity as the pH of the reflecting layer is adjusted to a value below the pKa of the optical filter agent. Once converted to its diminished light-absorbing form, the position of the optical filter agent with respect to the viewable image is not especially critical. It can, for example, be in front of the light-reflecting layer or preferably in the light-reflecting layer. In this preferred embodiment, the optical filter agent used should have good stability in aqueous alkali processing compositions and a high pKa, e.g., a pKa of 11 or more.

The optical filter agents of the present invention exhibit a substantial reduction in light-absorbing capacity upon conversion from a highly colored form at a pH above the pKa thereof to a pH below the pKa. Relative to the highly colored forms, the optical filter agents of the present invention are, thus, substantially non-absorbing in the visible region of the electromagnetic spectrum. Preferably, the optical filter agents will be colorless at a pH below the pKa and, accordingly, will be especially suited to the provision of a white or substantially white background for viewing of the transferred photographic image. Depending, however, upon the particular optical filter agent employed, the nature of substituent moieties present which may contribute light-absorbing capacity, or the concentration of such optical filter agent employed in a light-reflecting layer, a light-reflecting layer containing an optical filter agent of the invention may exhibit a coloration in its relatively and substantially non-absorbing form. The optical filter agents in their highly colored form provide, however, substantial protection of photosensitive elements against post-exposure fogging.

The particularly preferred light-reflecting pigment for film units of this invention is a titanium dioxide. In general, the coverage of the titanium dioxide should be such as to provide a percent reflectance of about 85–95%. Particularly preferred processing compositions for the above-described preferred embodiment and including the preferred titanium dioxide are those additionally having enough pH-sensitive optical filter agent to provide—on distribution—a layer having an optical transmission density $>\sim 6.0$ density units and an optical reflection density $>\sim 1.0$ density units at a pH above the pKa of the indicator dye(s).

The concentration of the optical filter agent of this invention used in film units to provide the desired opacification may be readily determined by routine testing. The concentration selected should be sufficient to provide— in combination with other layers between the photosensitive layer(s) and incident radiation—an optical transmission density sufficient to prevent the unwanted fogging during processing. The concentration of the optical filter agent(s) will, of course, vary as a function of, e.g., processing time, light intensity and exposure index. In general, the opacification system should provide an optical transmission density of at least about 5.0 and generally about 6.0 or 7.0 or somewhat higher.

The pH-sensitive optical filter agents of the invention can be utilized in an aqueous processing composition or layer of a film unit for provision of temporary opacification properties as previously described. In connection with such utilization, it may be advantageous to employ such optical filter agents in combination with other agents which provide desired opacification, such as other optical filter agents, or with other agents or materials which promote the desired function of the optical filter agents of the invention. Thus, depending upon the solubility characteristics of the particular pH-sensitive optical filter agent of the invention utilized for the provision of desired opacification, solvent materials for such agent may advantageously be utilized to increase solubility thereof in a processing composition or to facilitate coating or other formation of a suitable layer so as to thereby provide improved functionality of the pH-sensitive optical filter agent of the invention. Solvent materials such as dimethyl sulfoxide and dimethyl formamide can, for example, be utilized as solvents or solubilizing agents for optical filter agents of the invention for the provision of more efficient utilization of the agent. Other solvents can similarly be utilized for this purpose.

Figure 2:
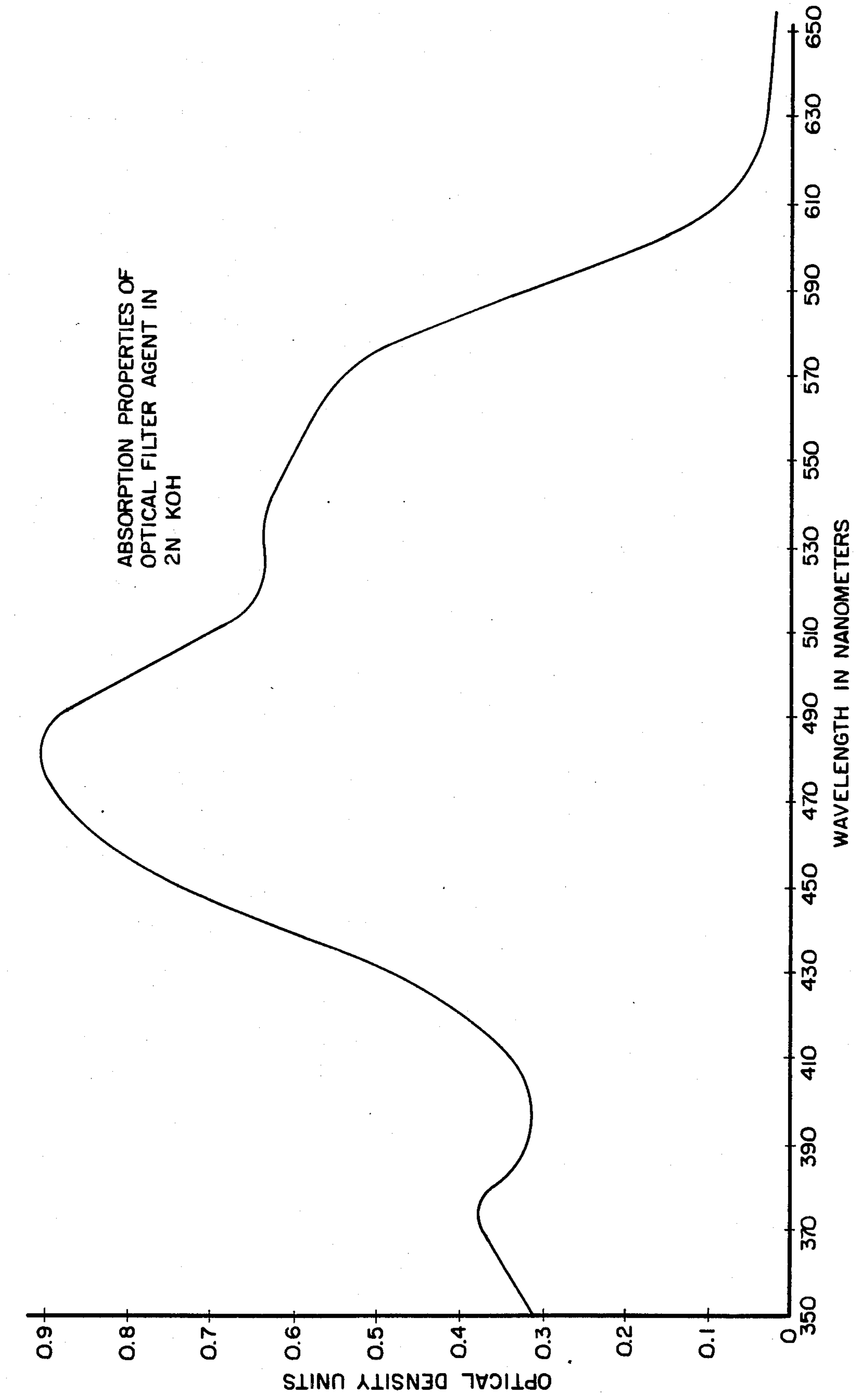
FIGS. 2 and 3 present graphic illustrations of spectral absorption characteristics of a pH-sensitive optical filter agent of this invention.
Figure 3:
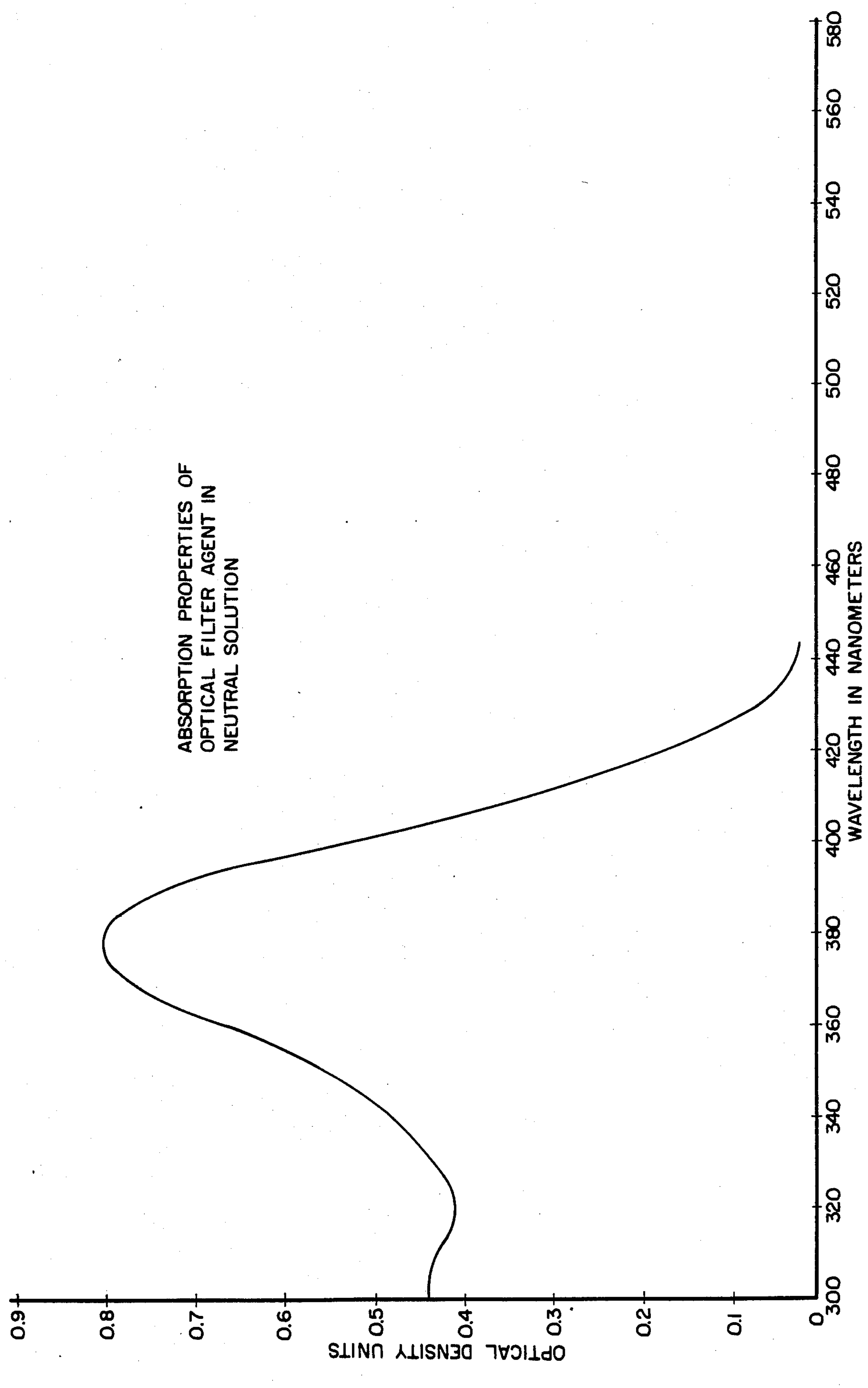

The pH-sensitive optical filter agents of this invention absorb radiation in the visible region of the spectrum. For example, the optical filter agents of the invention have been found to provide absorption for radiation in the green region (from about 500 nm to about 560 nm) of the visible spectrum. Some also provide absorption for radiation in the blue region as well (from about 460 nm to about 475 nm); others provide absorption for radiation in the green, blue, and also the red region (from about 640 nm to about 760 nm) of the visible spectrum. FIGS. 2 and 3 graphically illustrate absorption characteristics of a representative optical filter agent of this invention (the optical filter agent of Example 7 hereof). The Figures show the absorption densities of the optical filter agent in an alkaline solution at a pH above the pKa of the optical filter agent (FIG. 2) and at a neutral pH (FIG. 3). As shown in the Figures, and described in greater detail hereinafter in connection with Example 7, the optical filter agent of this invention provides at a pH above the pKa of the agent, an absorption capability for radiation in the visible region of the spectrum, and at neutral pH, a substantial reduction of such absorption.

In view of the possibly different absorption characteristics of individual optical filter agents, the selection of a particular agent of this invention will depend primarily on the spectral sensitivity of the silver halide emulsion layers of the film unit involved. For example, depending on the spectral sensitivity of the silver halide layers and the light conditions to which a film unit may be subjected during development, one or more optical filter agents of this invention may be utilized to protect the film unit from post-photoexposure fogging. Alternatively, selected optical filter agents may be used in combination with other known optical filter agents or indicator dyes to provide the requisite protective absorption.

Details relating to manners of making the optical filter agents of this invention and to methods for using them will be better appreciated by reference to the following examples.

EXAMPLE 1

In a 50-ml. Erlenmeyer flask, 0.81 g. of m-diacetylbenzene (0.005 mole), 2.89 g. of p(4-tolylsulfonyl)phenyl hydrazine (0.011 mole) and 10 ml. of ethanol were heated over a steam bath until a clear solution was obtained. Glacial acetic acid was added in a dropwise manner (3 drops) to catalyze the desired reaction. Upon cooling the reaction mixture in an ice bath, crystalline product was observed to form. The resulting product was collected by filtration and recrystallized from hot ethanol. The resulting product, the di-hydrazone of p(4-tolylsulfonyl)phenyl hydrazine and m-diacetyl benzene, had a melting point of 203°-205° C. and had the following structure:

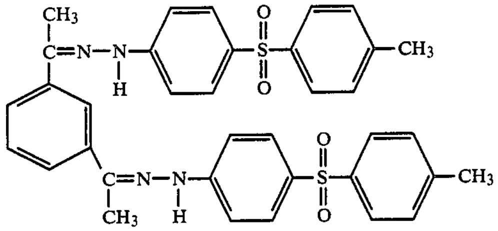

EXAMPLE 2

In a 50-ml. Erlenmeyer flask, 0.58 g. of acetone (0.01 mole) were mixed with 2.04 g. of 4-(methylsulfonyl)-phenyl hydrazine (0.011 mole) in 15 mls. of ethanol. The mixture was heated on a steam bath and a light-yellow solution was formed. Glacial acetic acid was added dropwise (3 drops) to the hot solution and the solution was then cooled in an ice bath. White crystals of the 4-(methylsulfonyl)phenyl hydrazone of acetone (having the structure set forth as Formula A hereinbefore) were collected by filtration and recrystallized from hot ethanol. The product had a melting point of 178°-180° C.

EXAMPLE 3

Utilizing the procedure of EXAMPLE 2 herein, the acetic acid-catalyzed reaction of 0.58 g. of acetone (0.01 mole) and 2.88 g. of p-(4-tolylsulfonyl)phenyl hydrazine (0.011 mole) in ethanol was conducted. The white crystalline product, recrystallized from hot ethanol, had a melting point of 166°-168° C. and had the structure set forth hereinbefore as Formula B.

EXAMPLE 4

Utilizing the procedure of EXAMPLE 2 herein, the acetic acid-catalyzed reaction of 0.6 g. of acetophenone (0.005 mole) and 1.12 g. of 4-(methylsulfonyl)phenyl hydrazine (0.006 mole) in 15 ml. of ethanol was conducted. The white crystalline product, recrystallized from hot ethanol, had a melting point of 210°-212° C. and had the structure set forth hereinbefore as Formula C.

EXAMPLE 5

Utilizing the procedure of EXAMPLE 2 herein, the acetic acid-catalyzed reaction of 0.6 g. of acetophenone (0.005 mole) and 1.57 g. of p-(4-tolylsulfonyl)phenyl hydrazine (0.006 mole) in ethanol was conducted. The resulting product, recrystallized from hot ethanol, was an off-white solid having a melting point of 173°-175° C. and having the structure set forth hereinbefore as Formula D.

EXAMPLE 6

Utilizing the procedure of EXAMPLE 2 herein, the acetic acid-catalyzed reaction of 0.81 g. of p-diacetyl benzene (0.005 mole) and 2.05 g. of 4-(methylsulfonyl)-phenyl hydrazine (0.011 mole) in ethanol was conducted. The resulting product, recrystallized from hot ethanol, was a yellow solid having a melting point above 240° C. and having the structure set forth hereinbefore as Formula E.

EXAMPLE 7

Utilizing the procedure of EXAMPLE 2 herein, the acetic acid-catalyzed reaction of 0.81 g. of p-diacetyl benzene (0.005 mole) and 2.89 g. of p-(4-tolylsulfonyl)-phenyl hydrazine (0.011 mole) in ethanol was conducted. The resulting product, recrystallized from hot ethanol, was a yellow solid having a melting point above 250° C. and having the structure set forth hereinbefore as Formula F.

The absorption properties of the hydrazone of Example 7 were measured under alkaline and neutral conditions as detailed hereinafter. In FIG. 2 is shown the absorption characteristics of the compound of Example 7 at a $10^{-4}$ Molar concentration in a 90:10 by weight mixture of 2 Normal potassium hydroxide and dimethylsulfoxide. As can be seen from FIG. 2, the presence of the compound of Example 7 in an alkaline medium above the pKa of the compound exhibits substantial absorption characteristics within the visible region of the electromagnetic spectrum. The absorption characteristics represented by FIG. 2 are illustrative of the "turned-on" or light-absorbing characteristics of an optical filter agent of the invention. From FIG. 3 can be seen the non-light absorbing or "turned-off" characteristics of an optical filter agent of the invention, the optical filter agent of Example 7. Thus, there is shown in FIG. 3, the absorption characteristics of the compound of Example 7 under the neutral pH condition of a $10^{-4}$ Molar concentration of the compound in dimethylsulfoxide solvent. As is apparent from the absorption characteristics represented in FIG. 3, the compound of Example 7 showed no appreciable absorption characteristics over the visible region of the electromagnetic spectrum.

EXAMPLE 8

Utilizing the procedure of EXAMPLE 2 herein, the acetic acid-catalyzed reaction of 2.24 g. of 1-hydroxyanthraquinone (0.01 mole) and 3.73 g. of 4-(methylsulfonyl)phenyl hydrazine (0.02 mole) in ethanol was conducted. The resulting product, recrystallized from hot ethanol, was a solid having a melting point of 183°-185° C. and having the structure set forth hereinbefore as Formula H.

EXAMPLE 9

Utilizing the procedure of EXAMPLE 2 herein, the acetic acid-catalyzed reaction of 5.96 g. of 4-(methylsulfonyl)phenyl hydrazine (0.032 mole) and 4.09 g. of 2-hydroxyacetophenone (0.03 mole) in ethanol was conducted. The resulting product, recrystallized from hot ethanol, was a yellow solid soluble in dimethyl sulfoxide, ethanol and acetone and had the structure set forth hereinbefore as Formula I.

EXAMPLE 10

Utilizing the procedure of EXAMPLE 2 herein, the acetic acid-catalyzed reaction of 4.95 g. of 4-nitroacetophenone (0.03 mole) and 5.6 g. of 4-(methylsulfonyl)phenyl hydrazine (0.032 mole) in ethanol was conducted. The resulting product, recrystallized from hot ethanol, was a yellow solid, soluble in dimethyl sulfoxide. The product had a melting point of 226° C. and had the structure set forth hereinbefore as Formula J.

EXAMPLE 11

Utilizing the procedure of EXAMPLE 2 herein, the acetic acid-catalyzed reaction of 1.35 g. of p-hydroxyacetophenone (0.01 mole) and 2.49 g. of p-(4-tolylsulfonyl)phenyl hydrazine (0.011 mole) in 50 mls. of ethanol was conducted. The resulting product, recrystallized from hot ethanol, had a melting point of above 200° C. and had the structure set forth hereinbefore as Formula G.

EXAMPLE 12

Utilizing the procedure of EXAMPLE 2 herein, the acetic acid-catalyzed reaction of 1.63 g. of 2-hydroxyacetophenone (0.012 mole) and 3.94 g. of p-(4-tolylsulfonyl)phenyl hydrazine (0.015 mole) in 50 mls. of ethanol was conducted. The resulting product, recrystallized from hot ethanol, was a yellow solid, soluble in dimethyl sulfoxide. The product had a melting point of above 200° C. and the following structure:

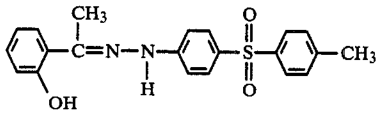

EXAMPLE 13

Utilizing the procedure of EXAMPLE 2 herein, the acetic acid-catalyzed reaction of 1.20 g. of acetophenone (0.01 mole) and 1.39 g. of p,p'-dihydrazinodiphenyl sulfone (0.005 mole) in 100 mls. of ethanol was conducted. The resulting product, recrystallized from hot ethanol, was a yellow solid, soluble in dimethyl sulfoxide, having a melting point of 175° C. and having the following structure:

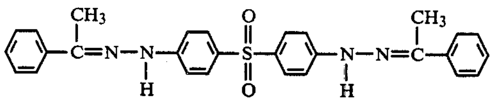

EXAMPLE 14

Utilizing the procedure of EXAMPLE 2 herein, the acetic acid-catalyzed reaction of 1.20 g. (0.01 mole) of acetophenone and 3.14 g. (0.012 mole) of 2,4-bis(methylsulfonyl)phenyl hydrazine in ethanol was conducted. The resulting product was recrystallized from hot ethanol and had a melting point of 186°-188° C. The product had the following structure:

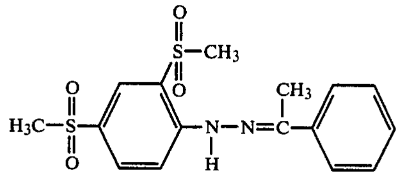

EXAMPLE 15

Utilizing the procedure of EXAMPLE 2 herein, the acetic acid-catalyzed reaction of 1.98 g. of 4-(methylsulfonyl)acetophenone (0.010 mole) and 2.05 g. of 4-(methylsulfonyl)phenyl hydrazine (0.011 mole) in ethanol was conducted. The resulting product, recrystallized from hot ethanol, was a yellow solid having the structure set forth hereinbefore as Formula L.

EXAMPLE 16

Utilizing the procedure of EXAMPLE 2 herein, the reaction of 3.60 g. of 9-fluorenone (0.02 mole) and 3.91 g. of 4-(methylsulfonyl)phenyl hydrazine (0.021 mole) in 50 mls. of ethanol was catalyzed with five drops of glacial acetic acid. The resulting product, recrystallized from hot ethanol, had a melting point of above 200° C. and had the following structure:

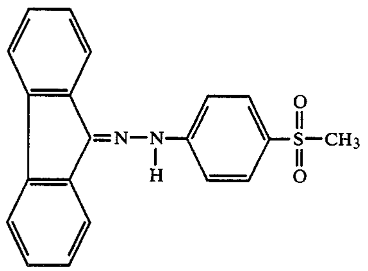

EXAMPLE 17

Utilizing the procedure of EXAMPLE 2 herein the p-nitrophenyl hydrazone of p-nitroacetophenone was prepared by reaction of 3.6 g. of p-nitroacetophenone (0.22 mole) and 3.0 g. of p-nitrophenyl hydrazine (0.20 mole) in 75 mls. of ethanol, catalyzed by 20 drops of glacial acetic acid. The product, recrystallized from hot ethanol, had a melting point of above 260° C. and the following structure:

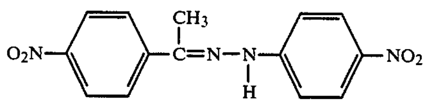

EXAMPLE 18

Utilizing the procedure of EXAMPLE 2 herein, the p-nitrophenyl hydrazone of the mono-oxime of 2,3-butanedione was prepared by the acetic acid-catalyzed reaction of equimolar proportions of the mono-oxime of 2,3-butanedione with p-nitrophenyl hydrazine. The recovered hydrazone product was a yellow solid having a melting point of 240° C. The product was soluble in 2N potassium hydroxide and exhibited a red color in solution. The hydrazone had the following structure:

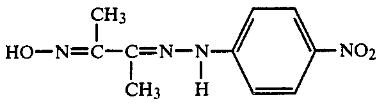

EXAMPLE 19

The following Example illustrates the use of a pH-sensitive optical filter agent of this invention in a film unit of the type disclosed in U.S. Pat. No. 3,415,644.

A film unit (comprising a photosensitive element, an image-receiving element and means for uniformly distributing an aqueous alkaline processing composition therebetween after photoexposure of the photosensitive element) was prepared as follows. A photosensitive element comprising an opaque polyethylene terephthalate film base containing the following layers, in sequence, was utilized:

1. A layer of cyan dye developer;
2. A red-sensitive gelatino-silver iodobromide emulsion;
3. A spacer layer;
4. A layer of magenta dye developer;
5. A green-sensitive gelatino silver iodobromide emulsion;
6. A spacer layer;
7. A layer of yellow dye developer;
8. A blue-sensitive gelatino-silver iodobromide emulsion; and
9. A gelatin overlayer.

As an image-receiving element there was employed a transparent polyethylene terephthalate film base carrying the following layers in sequence:

(1) a polymeric acid neutralizing layer;
(2) a polymeric spacer or timing layer; and
(3) a polymeric image-receiving layer or dyeable stratum.

Following photoexposure of the aforesaid photosensitive element to provide a developable image, the photoexposed element and the aforesaid image-receiving element were superposed in face-to-face relation with their respective supports outermost. A rupturable container retaining an alkaline processing composition was fixedly mounted between the respective superposed elements at the leading edge to provide a film unit. The rupturable container, comprised of an outer layer of lead foil and an inner layer of polyvinylchloride, was provided with a marginal seal of predetermined weakness such that passage of the leading edge of the film unit into and through a pair of pressure rollers would effect a rupture of such seal and uniform distribution of the aqueous processing composition between the elements of the film unit. The rupturable container positioned between the elements of the film unit retained an aqueous alkaline processing composition prepared by addition of 0.6 g. of the optical filter agent of EXAMPLE 2, in 1.3 cc. of dimethylsulfoxide, to 20 g. of the following composition:

-continued

| Components | Weight (grams) |
|---|---|
| Potassium hydroxide solution (10% by wt. conc.) | 20 ml. |
| Titanium dioxide | 12.0 |
| Viscosity-increasing agent - Oxime of poly(diacetone acrylamide) | 0.14 |
| N—phenethyl α-picolinium bromide | 0.44 |
| 3,5-dimethyl pyrazole | 0.06 |

A film unit of the invention as aforedescribed was processed in the following manner. The film unit (Film Unit A) was passed in the dark through a pair of rollers having a 0.0016 inch mechanical gap and allowed to remain in the dark for 30 seconds at which time the film unit was subjected to ambient light. From inspection of the resulting image it could be seen that the optical filter agent provided opacification to prevent fogging of the image. The following sensitometric results were obtained:

| | $D_{min}$ | | | $D_{max}$ | | |
|---|---|---|---|---|---|---|
| | R | G | B | R | G | B |
| Film Unit A (30" dark/room light) | 0.18 | 0.29 | 0.46 | 1.95 | 1.85 | 1.75 |

EXAMPLE 20

A film unit as described in Example 19 hereof was prepared, processed and evaluated in the manner described in Example 19, except that the aqueous alkaline processing composition of the film unit of this Example was prepared by the addition of 0.2 g. of the optical filter agent of Example 6, in 1.3 cc. of dimethyl sulfoxide, and three potassium hydroxide pellets (85% by weight and each weighing about 100 mgs.) to 20 g. of the following composition:

| Components | Weight (grams) |
|---|---|
| Potassium hydroxide solution (10% by wt. conc.) | 20 ml. |
| Titanium dioxide | 12.0 |
| Viscosity-increasing agent - Oxime of poly(diacetone acrylamide) | 0.14 |
| N—phenethyl α-picolinium bromide | 0.44 |
| 3,5-dimethyl pyrazole | 0.06 |

The film unit hereof was evaluated in the manner described in Example 19. The film unit (Film Unit B) was passed in the dark through a pair of rollers having a 0.0016 inch mechanical gap and immediately subjected to ambient room light. From inspection of the resulting image, it could be see that the optical filter agent provided protection against post-exposure fogging. The following sensitometric results were obtained:

| | $D_{min}$ | | | $D_{max}$ | | |
|---|---|---|---|---|---|---|
| | R | G | B | R | G | B |
| Film Unit B (Ambient room light) | 0.21 | 0.39 | 0.50 | 1.75 | 1.62 | 1.33 |

EXAMPLE 21

Film units as described in Example 19 hereof were prepared, processed and evaluated in the manner described in Example 19, except that the aqueous alkaline processing compositions of the respective film units of this Example (Film Units C and D) were prepared by addition, in the case of Film Unit C, of 0.2 g. of the optical filter agent of Example 7 in 1.33 cc. of dimethyl sulfoxide to 20 g. of the following composition, and in the case of Film Unit D, by the addition of 0.6 g. of the optical filter agent of Example 7 in 1.33 cc. of dimethyl sulfoxide to 20 g. of the following composition:

| Components | Weight (grams) |
|---|---|
| Potassium hydroxide solution (10% by wt. conc.) | 20 ml. |
| Titanium dioxide | 12.0 |
| Viscosity-increasing agent - Oxime of poly(diacetone acrylamide) | 0.14 |
| N—phenethyl α-picolinium bromide | 0.44 |
| 3,5-dimethyl pyrazole | 0.06 |

The film units hereof were evaluated in the manner described in Example 19. In the case of Film Unit C, the film unit was passed in the dark through a pair of rollers having a 0.0016 inch mechanical gap and immediately subjected to ambient room light. In the case of Film Unit D, the film unit was passed in the dark through the rollers and allowed to remain in the dark for 30 seconds at which time the film unit was subjected to ambient room light. The following sensitometric results were obtained:

| | $D_{min}$ | | | $D_{max}$ | | |
|---|---|---|---|---|---|---|
| | R | G | B | R | G | B |
| Film Unit C (ambient room light) | 0.18 | 0.29 | 0.43 | 0.61 | 1.16 | 1.24 |
| Film Unit D (30" dark/ambient room light) | 0.17 | 0.28 | 0.42 | 1.20 | 1.47 | 1.86 |

From inspection of the images obtained from Film Units C and D, it could be seen that the optical filter agent utilized therein provided protection against post-exposure fogging. A control film unit, utilizing a processing composition prepared by adding 1.3 cc. of dimethylsulfoxide (containing no optical filter agent) to 20 g. of the aforedescribed composition, was processed by passing the film unit in the dark through a pair of rollers having a 0.0016 inch mechanical gap and immediately subjecting the film unit to conditions of ambient light. The result was that the image was badly fogged. The following sensitometric results were obtained in the case of the control film unit.

| | $D_{min}$ | | | $D_{max}$ | | |
|---|---|---|---|---|---|---|
| | R | G | B | R | G | B |
| Control Film Unit (ambient room light) | 0.19 | 0.33 | 0.48 | 0.19 | 0.33 | 0.58 |

EXAMPLE 22

Film units as described in Example 19 hereof were prepared, processed and evaluated in the manner described in Example 19, except that the aqueous alkaline processing composition of the film units of this Example comprised the optical filter agent of Example 18 and had the following composition:

| Components | Weight (grams) |
|---|---|
| Optical Filter agent of Example 18 | 0.03 |
| Potassium hydroxide solution (10% by wt. conc.) | 20 ml. |
| Titanium Dioxide | 12.0 |
| Viscosity-increasing agent - Oxime of poly(diacetone acrylamide) | 0.14 |
| N—phenethyl α-picolinium bromide | 0.44 |
| 3,5-dimethyl pyrazole | 0.06 |

The film units hereof were evaluated in the manner described in Example 19. In one case, the film unit (Film Unit E) was passed in the dark through a pair of mechanical rollers having a 0.0016 inch gap and immediately subjected to ambient room light. In a second case, the film unit (Film Unit F) was passed in the dark through the same rollers but immediately thereafter subjected to a 10,000 foot-candle exposure for 30 seconds. The following results wee obtained:

| | $D_{min}$ | | | $D_{max}$ | | |
|---|---|---|---|---|---|---|
| | R | G | B | R | G | B |
| Film Unit E (ambient room light) | 0.13 | 0.19 | 0.36 | 2.01 | 1.81 | 1.83 |
| File Unit F (10,000 foot-candle exposure) | 0.13 | 0.18 | 0.36 | 0.63 | 0.84 | 1.18 |

A film unit (Control Film Unit) prepared in the manner of the film units of this example, but utilizing a processing composition to which no optical filter agent was added, was evaluated by passing the film unit in the dark through the rollers and immediately subjecting the film unit to an exposure of 10,000 foot-candles for 30 seconds. The film unit was badly fogged and provided the following sensitometric results:

| | $D_{Min}$ | | | $D_{max}$ | | |
|---|---|---|---|---|---|---|
| | R | G | B | R | G | B |
| Control Film Unit (ambient room light) | 0.12 | 0.18 | 0.25 | 0.12 | 0.18 | 0.25 |

From inspection of the sensitometric results indicated in connection with Film Units E and F, it can be seen that the optical filter agent utilized in Film Units E and F provided, relative to the control film unit, protection against post-exposure fogging.

What is claimed is:

1. A pH-sensitive optical filter agent providing light-absorbing capability at a pH above the pKa thereof and being substantially non-light-absorbing at a pH below the pKa thereof, said optical filter agent having the formula:

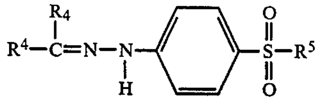

wherein each $R^4$ is a cyclic or acyclic hydrocarbon radical or a substituted cyclic or acyclic hydrocarbon radical, or both $R^4$ groups together complete a cyclic or polycyclic radical, or one or both of $R^4$ can present a hydrocarbon radical linking together one or more

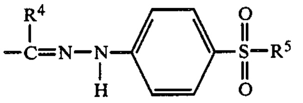

moieties; and $R^5$ is a cyclic or acyclic hydrocarbon radical or a substituted cyclic or acyclic hydrocarbon radical.

2. A pH-sensitive optical filter agent providing light-absorbing capability at a pH above the pKa thereof and being substantially non-light-absorbing at a pH below the pKa thereof, said optical filter agent having the formula

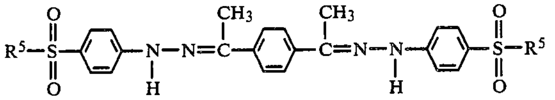

wherein each $R^5$ is selected from the group consisting of —$CH_3$ and

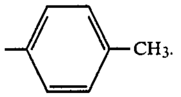

3. The optical filter agent of claim 1 having the formula:

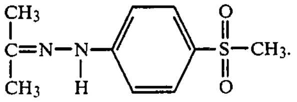

4. The optical filter agent of claim 1 having the formula:

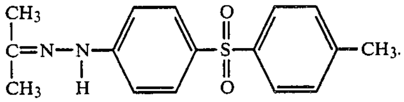

5. The optical filter agent of claim 1 having the formula:

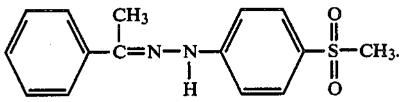

6. The optical filter agent of claim 1 having the formula:

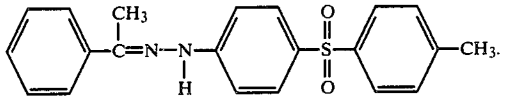

7. The optical filter agent of claim 2 having the formula:

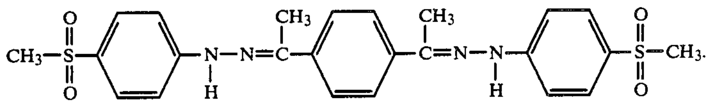

8. The optical filter agent of claim 2 having the formula:

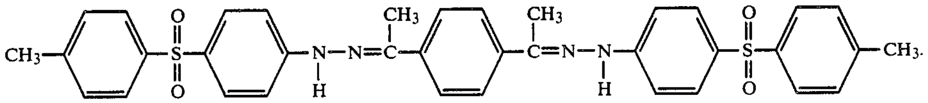

9. The optical filter agent of claim 1 having the formula:

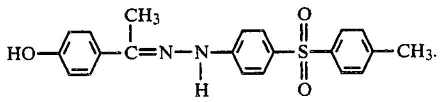

10. The optical filter agent of claim 1 having the formula

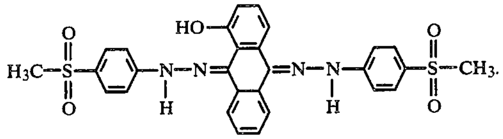

11. The optical filter agent of claim 1 having the formula:

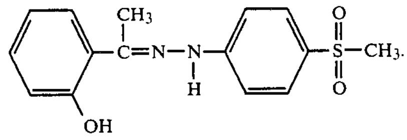

12. The optical filter agent of claim 1 having the formula:

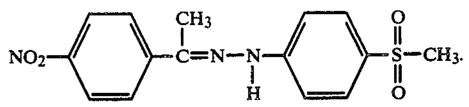

13. The optical filter agent of claim 1 wherein one said $R^4$ radical is alkyl of from 1 to 6 carbon atoms and the remaining said $R^4$ radical has the formula

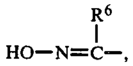
where $R^6$ is alkyl of from 1 to 6 carbon atoms.
14. The optical filter agent of claim 13 wherein each of $R^4$ and $R^6$ is methyl.
15. The optical filter agent of claim 1 wherein $R^5$ is selected from the group consisting of $—CH_3$ and
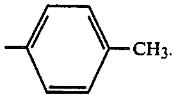
* * * * *